(12) United States Patent
Mansour et al.

(10) Patent No.: US 12,072,049 B2
(45) Date of Patent: *Aug. 27, 2024

(54) CONNECTOR COUPLING ASSEMBLY

(71) Applicant: CareFusion 303, Inc., San Diego, CA (US)

(72) Inventors: George Mansour, Diamond Bar, CA (US); Raymond P. Feith, Chino Hills, CA (US)

(73) Assignee: CareFusion 303, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/329,073

(22) Filed: Jun. 5, 2023

(65) Prior Publication Data

US 2023/0313928 A1 Oct. 5, 2023

Related U.S. Application Data

(63) Continuation of application No. 16/914,028, filed on Jun. 26, 2020, now Pat. No. 11,708,924.

(51) Int. Cl.
*F16L 37/091* (2006.01)
*A61M 39/10* (2006.01)
(Continued)

(52) U.S. Cl.
CPC ......... *F16L 37/091* (2013.01); *F16L 37/0985* (2013.01); *F16L 37/38* (2013.01); *A61M 39/1011* (2013.01); *A61M 2039/1027* (2013.01)

(58) Field of Classification Search
CPC ............ A61M 39/1011; A61M 39/105; A61M 39/1055; A61M 2039/1016;
(Continued)

(56) References Cited

U.S. PATENT DOCUMENTS 2,420,858 A 5/1947 Brownell
4,660,803 A * 4/1987 Johnston ............. F16L 37/0985
285/24
(Continued)

FOREIGN PATENT DOCUMENTS

EP 1678070 A2 7/2006
EP 1517723 B1 1/2007
(Continued)

OTHER PUBLICATIONS

Bangert, Bill, "Shorter times to blood transfusion associated with decreased death risk in trauma patients", Medical Xpress, Apr. 14, 2016, https://medicalxpress.com/news/2016-04-shorter-blood-transfusion-decreased-death.html.
(Continued)

*Primary Examiner* — Kevin F Murphy
*Assistant Examiner* — Jonathan J. Waddy
(74) *Attorney, Agent, or Firm* — Morgan, Lewis & Bockius LLP

(57) ABSTRACT

Couplers are described herein. A coupler includes a coupler body, a plurality of first retaining fingers, and a plurality of second retaining fingers. The coupler body includes a first end and a second end, and defining a cavity, the cavity configured to receive a first connector and a second connector. The plurality of first retaining fingers are configured to engage against a collar of the first connector to prevent axial motion of the first connector relative to the coupler. The plurality of second retaining fingers are configured to engage against a shoulder of the second connector with a retention force, and release the second connector by radially expanding in response to a pullout force exerted on the second connector exceeding the retention force.

17 Claims, 2 Drawing Sheets

(51) Int. Cl.
  *F16L 37/098* (2006.01)
  *F16L 37/38* (2006.01)
(58) Field of Classification Search
  CPC ............. A61M 2039/1027; A61M 2039/1077;
    A61M 2039/1083; A61M 2039/1088;
    F16L 37/091; F16L 37/098; F16L
    37/0985; F16L 37/133; F16L 37/38
  USPC ........................................................ 251/149
  See application file for complete search history.

(56) References Cited

U.S. PATENT DOCUMENTS

| | | |
|---|---|---|
| 5,176,406 A | 1/1993 | Straghan |
| 5,462,313 A | 10/1995 | Rea et al. |
| 5,542,717 A | 8/1996 | Rea et al. |
| 5,713,856 A | 2/1998 | Eggers et al. |
| 6,106,028 A | 8/2000 | Godeau et al. |
| 6,874,522 B2 | 4/2005 | Anderson et al. |
| 7,004,934 B2 | 2/2006 | Vaillancourt |
| 7,040,598 B2 | 5/2006 | Raybuck |
| 7,153,296 B2 | 12/2006 | Mitchell |
| 7,350,764 B2 | 4/2008 | Raybuck |
| 7,396,051 B2 | 7/2008 | Baldwin et al. |
| 7,763,013 B2 | 7/2010 | Baldwin et al. |
| 7,766,394 B2 | 8/2010 | Sage et al. |
| 7,794,675 B2 | 9/2010 | Lynn |
| 7,803,139 B2 | 9/2010 | Fangrow, Jr. |
| 7,803,140 B2 | 9/2010 | Fangrow, Jr. |
| 7,806,139 B2 | 10/2010 | Packham et al. |
| 7,815,614 B2 | 10/2010 | Fangrow, Jr. |
| 7,918,243 B2 | 4/2011 | Diodati et al. |
| 7,998,134 B2 | 8/2011 | Fangrow et al. |
| 8,123,738 B2 | 2/2012 | Vaillancourt |
| 8,142,418 B2 | 3/2012 | McMichael et al. |
| 8,211,069 B2 | 7/2012 | Fangrow, Jr. |
| 8,262,628 B2 | 9/2012 | Fangrow, Jr. |
| 8,361,408 B2 | 1/2013 | Lynn |
| 8,480,968 B2 | 7/2013 | Lynn |
| 8,777,908 B2 | 7/2014 | Fangrow, Jr. |
| 8,777,909 B2 | 7/2014 | Fangrow, Jr. |
| 8,795,256 B1 | 8/2014 | Smith |
| 8,888,758 B2 | 11/2014 | Mansour |
| 8,899,267 B2 | 12/2014 | Diodati et al. |
| 8,910,919 B2 | 12/2014 | Bonnal et al. |
| 8,974,425 B2 | 3/2015 | Tachizaki et al. |
| 8,974,437 B2 | 3/2015 | Williams et al. |
| 9,114,242 B2 | 8/2015 | Fangrow et al. |
| 9,126,028 B2 | 9/2015 | Fangrow et al. |
| 9,126,029 B2 | 9/2015 | Fangrow et al. |
| 9,192,753 B2 | 11/2015 | Lopez et al. |
| 9,234,616 B2 | 1/2016 | Carrez et al. |
| 9,358,379 B2 | 6/2016 | Fangrow, Jr. |
| 9,433,769 B2 | 9/2016 | Bayly |
| 9,468,749 B2 | 10/2016 | Mansour et al. |
| 9,492,649 B2 | 11/2016 | Carrez et al. |
| 9,636,492 B2 | 5/2017 | Fangrow, Jr. |
| 9,724,504 B2 | 8/2017 | Fangrow, Jr. et al. |
| 9,724,505 B2 | 8/2017 | Williams et al. |
| 9,861,805 B2 | 1/2018 | Dennis et al. |
| 9,933,094 B2 | 4/2018 | Fangrow |
| 9,974,939 B2 | 5/2018 | Fangrow, Jr. |
| 9,974,940 B2 | 5/2018 | Fangrow, Jr. |
| 10,029,086 B2 | 7/2018 | Nowak et al. |
| 10,156,306 B2 | 12/2018 | Fangrow |
| 10,173,045 B2 | 1/2019 | Mansour |
| 10,179,203 B1 | 1/2019 | Huslage et al. |
| 10,315,025 B2 | 6/2019 | Phillips et al. |
| 10,398,887 B2 | 9/2019 | Fangrow, Jr. et al. |
| 10,441,507 B2 | 10/2019 | Sanders |
| 10,518,078 B2 | 12/2019 | Stjernberg Bejhed et al. |
| 10,569,073 B2 | 2/2020 | Hallisey et al. |
| 10,625,068 B2 | 4/2020 | Leuthardt et al. |
| 10,655,768 B2 | 5/2020 | Jones et al. |
| 10,697,570 B2 | 6/2020 | Fangrow |
| 10,744,315 B2 | 8/2020 | Sanders |
| 10,842,982 B2 | 11/2020 | Fangrow, Jr. |
| 10,857,346 B2 | 12/2020 | Dennis et al. |
| 10,864,362 B2 | 12/2020 | Jones et al. |
| 10,881,847 B2 | 1/2021 | Lynn |
| 11,168,818 B2 | 11/2021 | Fangrow |
| 11,207,514 B2 | 12/2021 | Kakinoki |
| 11,235,135 B2 | 2/2022 | Tsai |
| 11,273,297 B2 | 3/2022 | Kakinoki |
| 11,484,471 B2 | 11/2022 | Sanders |
| 11,491,084 B2 | 11/2022 | Ueda et al. |
| 11,529,722 B2 | 12/2022 | Kujawski, Jr. et al. |
| 2004/0215158 A1 | 10/2004 | Anderson |
| 2005/0015075 A1* | 1/2005 | Wright .................. A61M 39/14 |
| | | 604/535 |
| 2005/0090805 A1 | 4/2005 | Shaw et al. |
| 2006/0129109 A1 | 6/2006 | Shaw et al. |
| 2007/0088292 A1 | 4/2007 | Fangrow, Jr. |
| 2007/0088293 A1 | 4/2007 | Fangrow, Jr. |
| 2007/0088294 A1 | 4/2007 | Fangrow, Jr. |
| 2007/0225635 A1 | 9/2007 | Lynn |
| 2008/0039803 A1 | 2/2008 | Lynn |
| 2008/0177237 A1 | 7/2008 | Stonehouse |
| 2011/0106046 A1 | 5/2011 | Hiranuma |
| 2014/0207118 A1* | 7/2014 | Tsoukalis ............... A61M 39/18 |
| | | 604/535 |
| 2014/0249487 A1 | 9/2014 | Lynn |
| 2014/0330254 A1 | 11/2014 | Rosenberger et al. |
| 2016/0000363 A1 | 1/2016 | Jones et al. |
| 2018/0200147 A1 | 7/2018 | Sanders |
| 2019/0184152 A1 | 6/2019 | Kakinoki |
| 2019/0282797 A1 | 9/2019 | Tsai |
| 2020/0113784 A1 | 4/2020 | Lopez et al. |
| 2020/0179672 A1 | 6/2020 | Kakinoki |
| 2020/0215319 A1 | 7/2020 | Fangrow, Jr. et al. |
| 2020/0284385 A1 | 9/2020 | Fangrow |
| 2020/0323734 A1 | 10/2020 | Ueda et al. |
| 2020/0338331 A1 | 10/2020 | Sanders |
| 2021/0069484 A1 | 3/2021 | Tsa |
| 2021/0077803 A1 | 3/2021 | Lynn |
| 2021/0252267 A1 | 8/2021 | Fangrow, Jr. |
| 2021/0388926 A1 | 12/2021 | Martin et al. |
| 2021/0393938 A1 | 12/2021 | Lynn et al. |
| 2022/0260189 A1 | 8/2022 | Deuse |
| 2022/0282814 A1 | 9/2022 | Fangrow |
| 2022/0288378 A1 | 9/2022 | Mermelshtein et al. |
| 2024/0115464 A1* | 4/2024 | Deckard ............ A61J 15/0015 |

FOREIGN PATENT DOCUMENTS

| | | |
|---|---|---|
| EP | 1622675 B1 | 8/2009 |
| EP | 2144634 A1 | 1/2010 |
| EP | 2298407 A1 | 3/2011 |
| EP | 2694132 A1 | 2/2014 |
| EP | 2562456 B1 | 6/2014 |
| EP | 2782633 A1 | 10/2014 |
| EP | 1842002 B1 | 4/2015 |
| EP | 2736582 B1 | 5/2015 |
| EP | 2089094 B1 | 1/2016 |
| EP | 2219721 B1 | 12/2017 |
| EP | 2753396 B1 | 12/2017 |
| EP | 2736584 B1 | 4/2018 |
| EP | 3305361 A1 | 4/2018 |
| EP | 2271398 B1 | 11/2018 |
| EP | 2480281 B1 | 11/2018 |
| EP | 2790750 B1 | 11/2018 |
| EP | 2331191 B1 | 3/2019 |
| EP | 3079756 B1 | 3/2019 |
| EP | 2121114 B1 | 5/2019 |
| EP | 2719419 B1 | 5/2019 |
| EP | 2956204 B1 | 8/2019 |
| EP | 3421077 B1 | 8/2019 |
| EP | 3530313 A1 | 8/2019 |
| EP | 3538201 A1 | 9/2019 |
| EP | 3570807 A1 | 11/2019 |
| EP | 3570809 A1 | 11/2019 |
| EP | 2536463 B1 | 4/2020 |

(56) References Cited

FOREIGN PATENT DOCUMENTS

| | | | |
|---|---|---|---|
| EP | 3381505 | B1 | 5/2020 |
| EP | 3538201 | B1 | 5/2020 |
| EP | 1904152 | B1 | 12/2020 |
| EP | 2150307 | B1 | 12/2020 |
| EP | 3313490 | B1 | 1/2021 |
| EP | 3760275 | A1 | 1/2021 |
| EP | 3851155 | A1 | 7/2021 |
| EP | 3517164 | B1 | 9/2021 |
| EP | 3954355 | A1 | 2/2022 |
| EP | 3960229 | A1 | 3/2022 |
| EP | 3973044 | A1 | 3/2022 |
| EP | 3305361 | B1 | 5/2022 |
| EP | 3134052 | B1 | 8/2022 |
| EP | 3530313 | B1 | 8/2022 |
| WO | WO-2006122406 | A1 | 11/2006 |
| WO | WO-2018022631 | A | 2/2018 |
| WO | WO-2021099437 | A1 | 5/2021 |
| WO | WO-2021180675 | A1 | 9/2021 |
| WO | WO-2021252197 | A1 | 12/2021 |
| WO | WO-2022042956 | A1 | 3/2022 |
| WO | WO-2022149339 | A1 | 7/2022 |
| WO | WO-2022207560 | A1 | 10/2022 |

OTHER PUBLICATIONS

Ivteam, "Force-activated separation IV connectors", 2022, Retrieved from the internet https://www.ivteam.com/intravenous-literature/force-activated-separation-iv-connectors/ [Last retrieved Jan. 13, 2023].

Lineus Medical, SafeBreak Product Features and Benefits Brochure, May 2021, mkg 0058 May 2021 Rev. 02.

Przen, "Lineus Medical Goes International, Signs ONEY for Distribution in Korea", PRZen Online Press Release Distribution, PrZen/33448014, MKG-0130 Rev 00, Retrieved from the internet https://przen.com/pr/lineus-medical-goes-international-signs-oney-for-distribution-in-korea-przen-33448014 [Last retrieved Jan. 13, 2023].

Rickard, et al., "Securing All intraVenous devices Effectively in hospitalised patients—the SAVE trial: study protocol for a multicentre randomised controlled trial", BMJ Open, Sep. 23, 2015;5(9):e008689, doi: 10.1136/bmjopen-2015-008689. PMID: 26399574; PMCID: PMC4593168.

Tada Group AB, LinkedIn Post "ReLink granted patent in Japan", LinkedIn, Mar. 2022, retrieved from the internet https://se.linkedin.com/company/tadamedical?trk=public_post_reshare_feed-actor-image&original_referer= [Last retrieved Mar. 2022].

International Search Report and Written Opinion for Application No. PCT/US2021/039238, dated Oct. 7, 2021, 13 pages.

\* cited by examiner though an arrangement of flexible tubing and fittings, commonly referred to as an "IV set," to a source of fluid, for example, an IV bag. Often, tubing or catheters are coupled or secured to each other to allow fluid communication between various portions of tubing or catheters.

CONNECTOR COUPLING ASSEMBLY

CROSS REFERENCE TO RELATED APPLICATION

This application is a continuation of U.S. patent application Ser. No. 16/914,028, entitled "CONNECTOR COUPLING ASSEMBLY", filed Jun. 26, 2020, the disclosure of which is incorporated herein by reference in its entirety.

FIELD OF THE INVENTION

Background

Medical treatments often include the infusion of a medical fluid (e.g., a saline solution or a liquid medication) to patients using an intravenous (IV) catheter that is connected though an arrangement of flexible tubing and fittings, commonly referred to as an "IV set," to a source of fluid, for example, an IV bag. Often, tubing or catheters are coupled or secured to each other to allow fluid communication between various portions of tubing or catheters.

In some applications, such tubing or catheters may become dislodged due to improper securement and/or when the coupling is subject to forces greater than what the coupling is designed to withstand.

SUMMARY

The disclosed subject matter relates to connector couplers. In certain embodiments, a coupler is disclosed that comprises a coupler body comprising a first end and a second end, and defining a cavity, the cavity configured to receive a first connector and a second connector; a plurality of first retaining fingers disposed adjacent to the first end and extending radially inward into the cavity, wherein the plurality of first retaining fingers are radially biased inward toward the cavity and are configured to engage against a collar of the first connector to prevent axial motion of the first connector relative to the coupler; a plurality of second retaining fingers disposed at the second end and extending radially inward into the cavity, wherein the plurality of second retaining fingers are radially biased inward toward the cavity and are configured to: engage against a shoulder of the second connector with a retention force; and release the second connector by radially expanding in response to a pullout force exerted on the second connector exceeding the retention force.

In certain embodiments, a coupler assembly is disclosed that comprises a first connector, comprising: a first connector body with a first inlet configured to be coupled to a first portion of tubing and a first outlet in fluid communication with the first inlet; and a collar disposed between the first inlet and the first outlet, wherein the collar radially extends from the first connector body; a second connector, comprising: a second connector body with a second inlet configured to be releasably coupled with the first outlet of the first connector, and a second outlet configured to be coupled to a second portion of tubing and in fluid communication with the second inlet; and a shoulder disposed between the second inlet and the second outlet, wherein the shoulder radially extends from the second connector body; and a coupler, comprising: a coupler body comprising a first end and a second end, and defining a cavity, wherein the first connector and the second connector are at least partially disposed within the cavity; a plurality of first retaining fingers disposed adjacent to the first end and extending radially inward into the cavity, wherein the plurality of first retaining fingers are radially biased inward to engage against the collar of the first connector to prevent axial motion of the first connector relative to the second connector; and a plurality of second retaining fingers disposed at the second end and extending radially inward into the cavity, wherein the plurality of second retaining fingers are radially biased inward engage against the shoulder of the second connector with a retention force, and the plurality of second retaining fingers are configured to release the second connector by radially expanding in response to a pullout force exerted on the second connector exceeding the retention force.

In certain embodiments, a method is disclosed that comprises inserting a portion of a first connector into a cavity of a coupler, wherein the first connector is coupled to a first portion of tubing; biasing a plurality of first retaining fingers radially inward to engage against a collar of the first connector; inserting a portion of a second connector into the cavity from an opposite end of the coupler, wherein the second connector is coupled to a second portion of tubing; coupling an outlet of the first connector with an inlet of the second connector, permitting fluid communication between the first portion of tubing and the second portion of tubing; and biasing a plurality of second retaining fingers radially inward to engage against a shoulder of the second connector with a retention force.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

Figure 1:
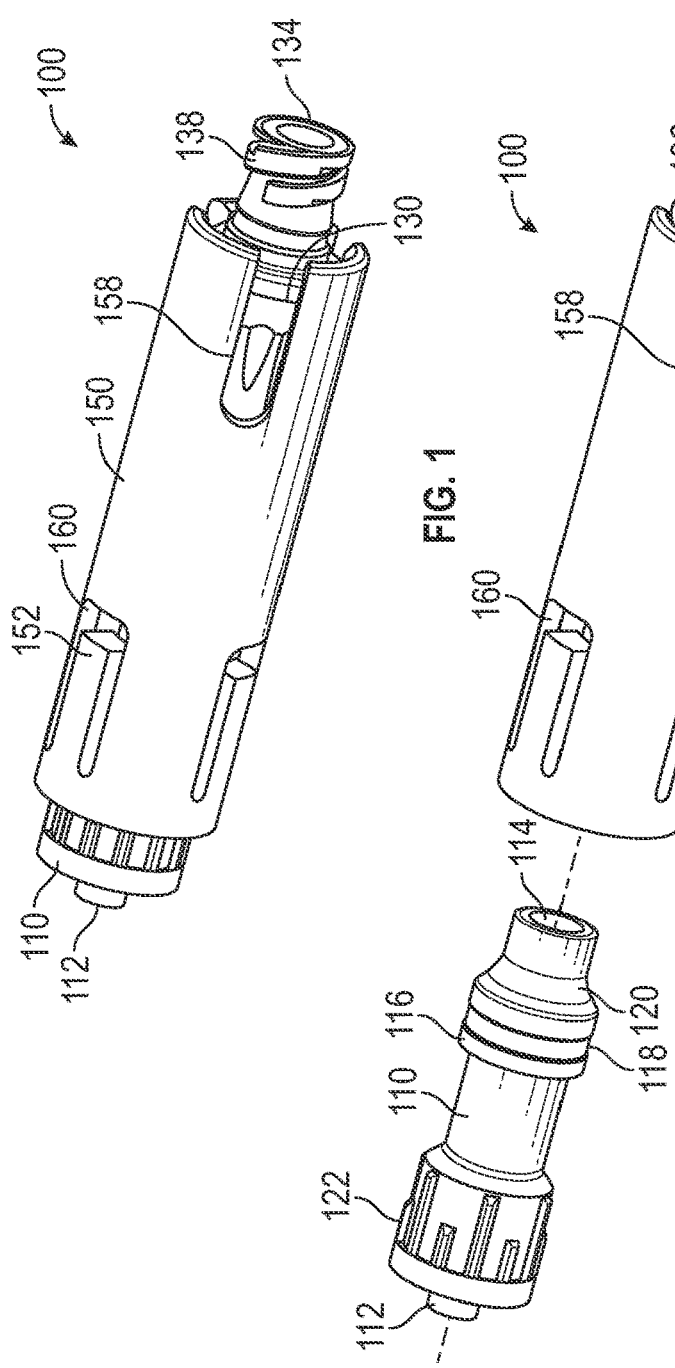
FIG. 1 is a perspective view of a coupler assembly, in accordance with various aspects of the present disclosure.

The disclosed coupler incorporates a plurality of first retaining fingers and a plurality of second retaining fingers. The plurality of first retaining fingers can be configured to engage against a collar of the first connector to prevent axial motion of the first connector. The plurality of second retaining fingers can be configured to engage against the shoulder of the second connector, preventing axial motion of the second connector. By preventing axial motion of the first and second connectors, the coupler can prevent unintended or accidental dislodgement of the first and second connectors. Further, the plurality of second retaining fingers can be configured to release the second connector in response to a pullout force. By allowing the second connector to be removed in response to a pullout force, the second connector can be removed if needed by applying an increased pullout force.

The detailed description set forth below is intended as a description of various configurations of the subject technology and is not intended to represent the only configurations in which the subject technology may be practiced. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding. Reference numbers may have letter suffixes appended to indicate separate instances of a common element while being referred to generically by the same number without a suffix letter.

While the following description is directed to the connection of medical fittings for the administration of medical fluid using the disclosed coupler, it is to be understood that this description is only an example of usage and does not limit the scope of the claims. Various aspects of the disclosed coupler may be used in any application where it is desirable to secure the connection of various tubing and fittings.

The disclosed coupler overcomes several challenges discovered with respect to certain conventional couplers. One challenge with certain conventional couplers is that certain conventional couplers may be improperly secured. Further, during use, certain conventional couplers may be designed to release or dislodge in response to relatively low pullout forces. For example, certain conventional couplers may release in response to pullout forces experienced during patients rolling over in bed, patients catching tubing or lines on bed rails, moving patients to a different bed, fidgeting by pediatric patients, and/or disoriented adult patients pulling out their lines. Indeed, the Association for Vascular Access (AVA) Annual Scientific Meeting in 2017 reported a 10% dislodgement rate for 1,000 patients fitted with peripheral IV catheters, translating to approximately 33 million dislodgements per year in the U.S. alone. Because the accidental or unintentional dislodgement of tubing, catheters, or fittings may interrupt the administration of medical fluids, the use of certain conventional couplers is undesirable.

Therefore, in accordance with the present disclosure, it is advantageous to provide a coupler as described herein that allows for improved securement of fittings or connectors. The disclosed coupler provides a plurality of first retaining fingers and a plurality of second retaining fingers that permits the secure retention of the connectors, while allowing intentional removal of the connector as required.

Examples of couplers that allow secure retention of connectors are now described.

Figure 2:
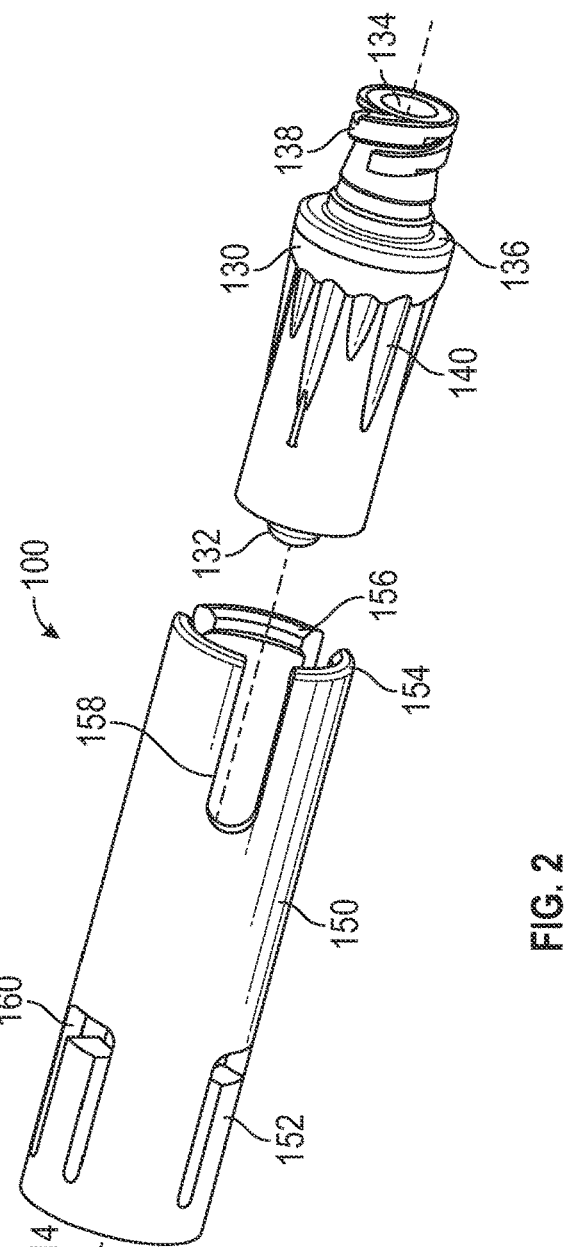
FIG. 2 is an exploded perspective view of the coupler assembly of FIG. 1, in accordance with various aspects of the present disclosure.

FIG. 1 is a perspective view of a coupler assembly 100, in accordance with various aspects of the present disclosure. FIG. 2 is an exploded perspective view of the coupler assembly 100 of FIG. 1, in accordance with various aspects of the present disclosure. With reference to FIGS. 1 and 2, the coupler assembly 100 allows the flow of a fluid, such as a medical fluid, from a fluid source to a patient by releasably coupling a portion of tubing or line with another portion of tubing or line in fluid communication.

In the depicted example, portions of tubing can be terminated with connectors, such as an upper connector 110 and/or a lower connector 130. The upper connector 110 and/or the lower connector 130 can allow for the connection and/or disconnection of tubing to allow for selective fluid communication therebetween.

As illustrated, a first portion of tubing can be terminated by the upper connector 110 to allow the first portion of tubing to be connected and/or disconnected with a mating connector, such as the lower connector 130. In some embodiments, a portion of tubing can be coupled with, or engage with an inlet 112 of the upper connector 110. The inlet 112 can be in fluid communication with the tubing to allow fluid to pass through the upper connector 110. In some embodiments, the inlet 112 can have a flat surface to allow for clinicians to easily clean and disinfect the inlet 112. Fluid can exit or flow through the upper connector 110 via an outlet 114 disposed opposite to the inlet 112. The flow path through the upper connector 110 can have a straight fluid pathway to make flushing easier and to reduce the risk of hemolysis. Optionally, the upper connector 110 can include raised features 122 disposed on the surface of the upper connector 110 to allow a clinician to more easily handle or manipulate the upper connector 110. Some embodiments of the upper connector 110 can provide connectors that are compatible with connectors of other portions of fluid delivery systems. Examples of the upper connector 110 can include the SmartSite™ connector, the Max Zero connector, and the MaxPlus connector.

Similarly, a second portion of tubing can be terminated by the lower connector 130 to allow the second portion of tubing to be connected and/or disconnected with a mating connector, such as the upper connector 110. In some embodiments, a portion of tubing can be coupled with, or engage with an outlet 134 of the lower connector 130. In some embodiments, the outlet 134 can include a threaded luer connection 138 to facilitate coupling with tubing.

The tubing can be in fluid communication with the outlet 134 to allow the tubing to receive flow passing through the lower connector 130. The lower connector 130 can receive fluid flow from the inlet 132 disposed opposite to the outlet 134. In some embodiments, the lower connector 130 can include a no-drip feature to prevent leaks or surface contamination. The lower connector can further include a luer lock to prevent accidental discharges. Optionally, the lower connector 130 can include raised features 140 disposed on the surface of the lower connector 130 to allow a clinician to more easily handle or manipulate the lower connector 130. Examples of the lower connector 130 can include the Texium® connector.

In some embodiments, the outlet 114 of the upper connector 110 and/or the inlet 132 of the lower connector 130 can include features that allow for the outlet 114 to mate with an inlet 132. For example, the outlet 114 can fit together or otherwise engage with the inlet 132 to allow fluid communication between the upper connector 110 and the lower connector 130 and the portions of tubing coupled thereto. As can be appreciated, the upper connector 110 and the lower connector 130 can be coupled and decoupled to permit fluid communication as desired. As illustrated, the outlet 114 can include an outer portion that is smooth and otherwise free from threads. The outlet 114 can include an outer portion that includes threads to facilitate coupling with the lower connector 130. As can be appreciated, the upper connector 110 can couple with the lower connector 130 to provide needle free connections. Advantageously, the upper connector 110 can pair with a lower connector to form a leak-free closed system, allowing the delivery of hazardous drugs. For example, a SmartSite™ connector can connect to a Texium® connector to provide a closed system that prevents hazardous drugs from leaking or dripping.

In some embodiments, the upper connector 110 can include a sealing valve to allow for flow to pass therethrough when the outlet 114 is coupled to a mating connector, and can prevent or restrict flow when the upper connector 110 is disconnected from a mating connector. In some embodiments, the upper connector 110 can include a sealing valve to seal the flow path between the inlet 112 and the outlet 114 when the outlet 114 is uncoupled from a mating connector. The sealing valve can be moved to an open position when a mating connector is coupled to the outlet 114, allowing flow between the inlet 112, the outlet 114, and into the mating connector.

Similarly, the lower connector 130 can include a sealing valve to allow for flow to pass therethrough when the inlet 132 is coupled to a mating connector, and can prevent or restrict flow when the lower connector 130 is disconnected from a mating connector. The lower connector 130 may include a sealing valve to seal the flow path between the inlet 132 and the outlet 134 when the inlet 132 is uncoupled from a mating connector. Further, the sealing valve can be moved to an open position when a mating connector is coupled to the inlet 132, allowing flow into the lower connector 130 and between the inlet 132 and the outlet 134. Some embodiments provide that portions of the sealing valve can be formed from silicone.

Figure 3:
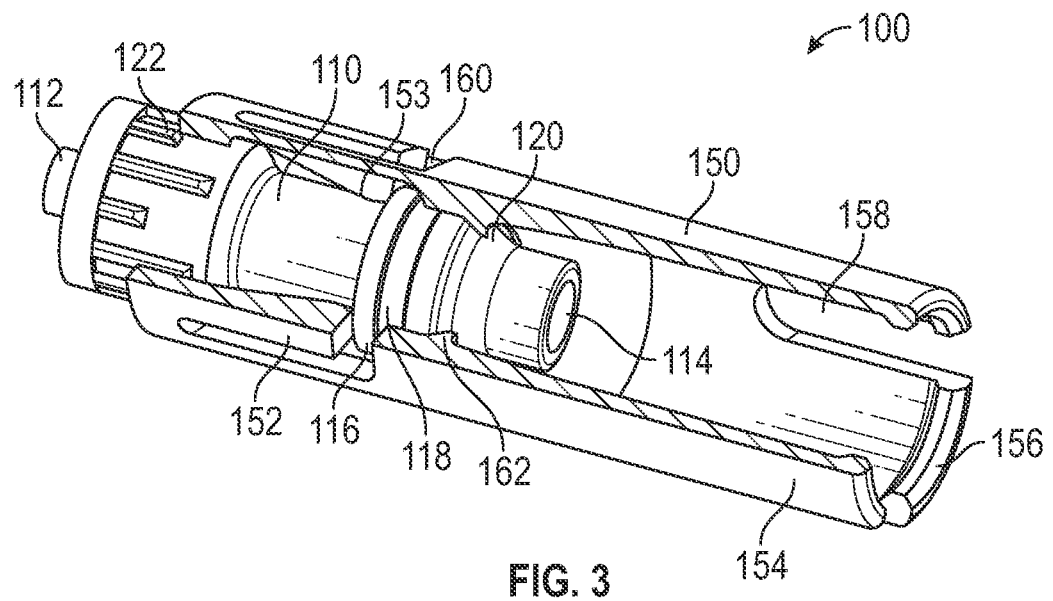
FIG. 3 is a cross-sectional view of the coupler assembly of FIG. 1 with the second connector omitted, in accordance with various aspects of the present disclosure.

FIG. 3 is a cross-sectional view of the coupler assembly 100 of FIG. 1 with the lower connector 130 omitted, in accordance with various aspects of the present disclosure. With reference to FIGS. 1-3, the coupler 150 can secure the upper connector 110 and the lower connector 130 in a coupled position to allow secured fluid communication therebetween that may not be accidently or unintentionally interrupted. In the depicted example, the coupler 150 can retain or secure the upper connector 110 and/or the lower connector 130 by engaging with features of the upper connector 110 and/or the lower connector 130.

As illustrated, the coupler 150 can have a generally tubular body, extending between a first end configured to receive the upper connector 110 and a second end configured to receive the lower connector 130. The coupler 150 can define a cavity therein, which allows for portions of the upper connector 110 and/or the lower connector 130 to be disposed within the coupler 150.

In the depicted example, the upper connector 110 can be inserted into the cavity of the coupler 150 to engage with the coupler 150 and prevent unwanted dislodgment of the upper connector 110. As illustrated, the outlet 114 end of the upper connector 110 is guided into the cavity through a first end of the coupler 150 to a desired axial position relative to the coupler 150. For example, the upper connector 110 can be axially positioned within the coupler 150 to allow the outlet 114 to engage or couple with the inlet 132 of the lower connector 130, when the lower connector 130 is inserted. Advantageously, the upper connector 110 can be axially positioned within the coupler 150, such that the outlet 114 is recessed within the cavity, preventing touch contamination of the outlet 114 by patients, clinicians, etc., when the upper connector 110 is not coupled to the lower connector 130.

In some embodiments, features within the coupler 150 can position the upper connector 110 within the cavity of the coupler 150. Optionally, the coupler 150 can include a tapered alignment feature 162 to radially align the outlet 114 and/or the upper connector 110 generally within the cavity of the coupler 150. The tapered alignment feature 162 can extend from the walls of the coupler 150 into the cavity and have a generally conical shape that radially converges. Therefore, as the upper connector 110 is inserted or advanced into the coupler 150, the tapered alignment feature 162 can radially guide the upper connector 110 within the cavity.

In some embodiments, the upper connector 110 can include a frustroconical or tapered portion 120 to engage or interface with the tapered alignment feature 162 of the coupler 150. The tapered portion 120 can slide along the tapered alignment feature 162 to radially align the upper connector 110 within the coupler 150. The tapered portion 120 can be disposed between the inlet 112 and the outlet 114 of the upper connector 110. In some embodiments, the tapered portion 120 can be disposed near the outlet 114 of the upper connector 110.

As the upper connector 110 is inserted into the coupler 150, features of the coupler 150 can retain the upper connector 110 in the inserted position. In some embodiments, the coupler 150 can axially retain the upper connector 110, while permitting the upper connector 110 to rotate relative to the coupler 150. Optionally, the coupler 150 can rotationally retain the upper connector 110 relative to the coupler 150.

In the depicted example, the coupler 150 can include a plurality of first retaining fingers 152 to engage or retain the upper connector 110 in the inserted or coupled axial position. In some embodiments, the plurality of first retaining fingers 152 are radially movable to allow the upper connector 110 to be inserted into the coupler 150. The plurality of first retaining fingers 152 can move in and out of the cavity defined by the coupler 150.

As illustrated, the plurality of first retaining fingers 152 can be hinged relative to the coupler 150 body. In some embodiments, the plurality of first retaining fingers 152 are integrally formed with the coupler 150. Optionally, slots or windows 160 are cut around the material of the coupler 150 to form the plurality of first retaining fingers 152. The plurality of first retaining fingers 152 can be circumferentially spaced apart around the coupler 150. Optionally, the plurality of first retaining fingers 152 can be disposed in groups or sets around the coupler 150. In some embodiments, the plurality of first retaining fingers 152 can be spaced apart from the end of the coupler 150 that receives the upper connector 110.

In the depicted example, the plurality of first retaining fingers 152 can be biased radially inward to engage or retain the upper connector 110 within the coupler 150. The plurality of first retaining fingers 152 can apply a radial spring force against the upper connector 110 to retain the upper connector 110 within the coupler 150. As can be appreciated, the spring force of the plurality of first retaining fingers 152 can correspond to the retention force exerted upon the upper connector 110. The plurality of first retaining fingers 152 can elastically deform to engage against the upper connector 110.

In some embodiments, the plurality of first retaining fingers 152 can each include a protrusion or protruding feature 153 to engage with features of the upper connector 110. The protruding feature 153 can extend radially inward to contact the upper connector 110. For example, the plurality of first retaining fingers 152 and/or the protruding feature 153 can engage against a collar 116 of the upper connector 110.

Optionally, the upper connector 110 can include a collar 116 that can be a radially raised portion that extends from the upper connector 110. The collar 116 can be disposed between the inlet 112 and the outlet 114. As illustrated, the collar 116 can be disposed toward the outlet 114. Optionally, the collar 116 can include a groove or recess 118 disposed within the collar 116.

In the depicted example, the plurality of first retaining fingers 152 and/or the protruding feature 153 can engage against the collar 116 to prevent axial movement of the upper connector 110 relative to the coupler 150. During insertion, after the collar 116 moves past the plurality of first retaining fingers 152 and/or the protruding feature 153, the plurality of first retaining fingers 152 can move radially inward, axially bearing against the axial surface of the collar 116 and thereby retaining the upper connector 110. In some embodiments, the protruding feature 153 of each of the plurality of first retaining fingers 152 can engage against the collar 116. Optionally, the protruding feature 153 can have a generally square or axial-facing surface bearing against the collar 116, preventing radial expansion of the plurality of first retaining fingers 152 in response to axial (pullout) force exerted against the upper connector 110.

Figure 4:
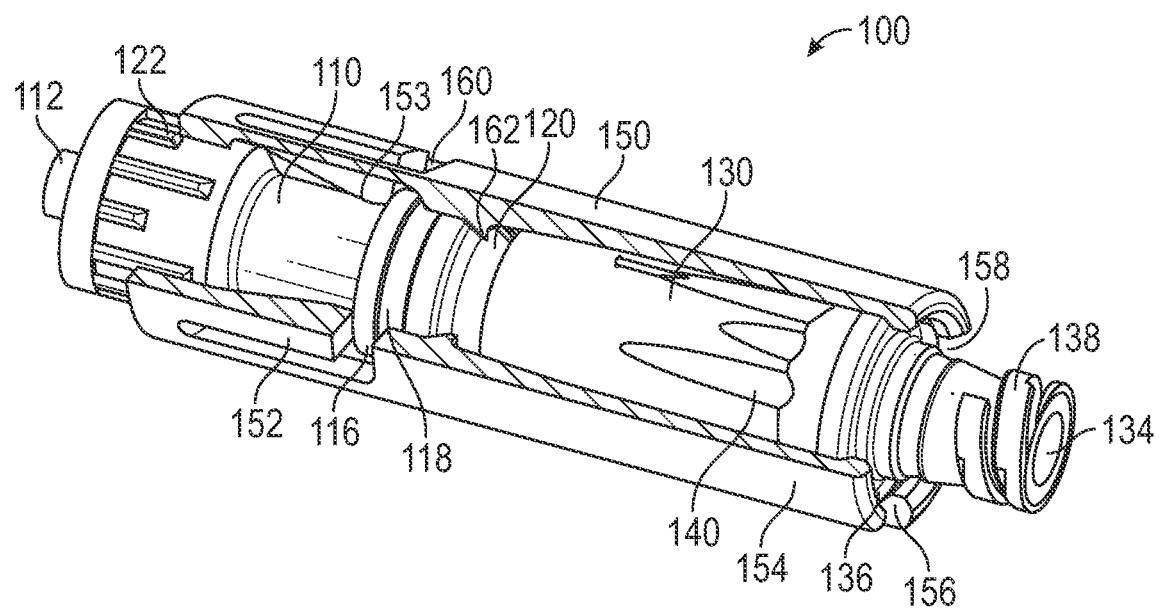
FIG. 4 is a cross-sectional view of the coupler assembly of FIG. 1, in accordance with various aspects of the present disclosure.

FIG. 4 is a cross-sectional view of the coupler assembly 100 of FIG. 1, in accordance with various aspects of the present disclosure. With reference to FIGS. 1-4, in the depicted example, the lower connector 130 can be inserted into the cavity of the coupler 150 to engage with the coupler 150 and the upper connector 110 and to prevent or resist unwanted dislodgment with the upper connector 110. As illustrated, the inlet 132 end of the lower connector 130 is guided into the cavity through a second end of the coupler 150 to a desired axial position relative to the coupler 150. For example, lower connector 130 can be axially positioned within the coupler 150 to allow the inlet 132 to engage or couple with the outlet 114 of the upper connector 110. In some embodiments, features within the coupler 150 can position lower connector 130 within the cavity of the coupler 150.

As the lower connector 130 is inserted into the coupler 150, features of the coupler 150 can retain the lower connector 130 in the inserted position. In some embodiments, the coupler 150 can axially retain the lower connector 130, while permitting the lower connector 130 to rotate relative to the coupler 150 and the upper connector 110. Optionally, the coupler 150 can rotationally retain the lower connector 130 relative to the coupler 150.

In the depicted example, the coupler 150 can include a plurality of second retaining fingers 154 to engage or retain the lower connector 130 in the inserted or coupled axial position. In some embodiments, the plurality of second retaining fingers 154 are radially movable to allow the lower connector 130 to be inserted into the coupler 150. The plurality of second retaining fingers 154 can move in and out of the cavity defined by the coupler 150.

As illustrated, the plurality of second retaining fingers 154 can be hinged relative to the coupler 150 body. In some embodiments, the plurality of second retaining fingers 154 are integrally formed with the coupler 150. Slots or windows 158 may be cut between the material of the coupler 150 to form the plurality of second retaining fingers 154. The plurality of second retaining fingers 154 can be circumferentially spaced apart around the coupler 150. The plurality of second retaining fingers 154 can be disposed in groups or sets around the coupler 150. In some embodiments, the plurality of second retaining fingers 154 can be disposed at the end of the coupler 150 that receives the lower connector 130.

In the depicted example, the plurality of second retaining fingers 154 can be biased radially inward to engage or retain the lower connector 130 within the coupler 150. The plurality of second retaining fingers 154 can apply a radial spring force against the lower connector 130 to retain the lower connector 130 within the coupler 150. As can be appreciated, the spring force of the plurality of second retaining fingers 154 can correspond to the retention force exerted upon the lower connector 130. The plurality of second retaining fingers 154 can elastically deform to engage against the lower connector 130.

In some embodiments, the plurality of second retaining fingers 154 can each include a protrusion or protruding feature 156 to engage with features of the lower connector 130. The protruding feature 156 can extend radially inward to contact the lower connector 130. For example, the plurality of second retaining fingers 154 and/or the protruding feature 156 can engage against a shoulder 136 of the lower connector 130.

Optionally, the lower connector 130 can include a shoulder 136 that can be a radially raised portion that extends from the lower connector 130. The shoulder 136 can be disposed between the inlet 132 and the outlet 134. As illustrated, the shoulder 136 can be disposed toward the outlet 134.

In the depicted example, the plurality of second retaining fingers 154 and/or the protruding feature 156 can engage against the shoulder 136 to prevent or restrict axial movement of the lower connector 130 relative to the coupler 150. During insertion, after the shoulder 136 moves past the plurality of second retaining fingers 154 and/or the protruding feature 156, the plurality of second retaining fingers 154 can move radially inward, axially bearing against the axial surface of the shoulder 136 and thereby retaining the lower connector 130. In some embodiments, the protruding feature 156 of each of the plurality of second retaining fingers 154 can engage against the shoulder 136.

Optionally, the protruding feature 156 can have a generally ramped surface bearing against the shoulder 136, permitting radial expansion of the plurality of second retaining fingers 154 in response to axial (pullout) force exerted against the lower connector 130. In some embodiments, the coupler 150 can be configured to allow the lower connector 130 to be removed in response to a selected or predetermined pullout force. The lower connector 130 may be removed from the coupler 150 with a pullout force of 1 pound, 2 pounds, 4 pounds, 5 pounds, 10 pounds, etc. As can be appreciated, the pullout force can be selected to prevent inadvertent release, while preventing damage to tubing or harm to patients.

Optionally, the coupler 150 can be configured to allow the upper connector 110 to remain retained when the lower connector 130 is removed. In other words, the coupler 150 can be configured to allow the lower connector 130 to be released with a lower pullout force compared to the upper connector 110. After removal, the lower connector 130 can be reinserted into the coupler 150 to reconnect the lower connector 130 with the upper connector 110.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A method, comprising:
   inserting a portion of a first connector into a cavity of a coupler, wherein the first connector is coupled to a first portion of tubing;
   biasing a plurality of first retaining fingers disposed at a first end of the coupler to engage against a collar of the first connector;
   inserting a portion of a second connector into the cavity from a second end of the coupler, wherein a second outlet of the second connector is threadedly engaged with a second portion of tubing;
   coupling an outlet of the first connector with an inlet of the second connector, permitting fluid communication between the first portion of tubing and the second portion of tubing;
   biasing a plurality of second retaining fingers of the coupler to engage against a shoulder of the second connector with a retention force;
   exerting a pullout force on the second connector in excess of the retention force; and
   releasing the second connector from the coupler in response to the pullout force in excess of the retention force.

2. The method of claim 1, further comprising:
   radially aligning the portion of the first connector within the cavity of the coupler.

3. The method of claim 1, further comprising:
   radially aligning the first connector within the cavity of the coupler via a tapered portion within the cavity.

4. The method of claim 1, wherein each of the plurality of second retaining fingers comprises a ramped protrusion extending radially inward.

5. The method of claim 1, further comprising:
permitting rotational motion of the first connector relative to the coupler.

6. The method of claim 1, wherein the coupler comprises a tubular shape.

7. A coupler assembly comprising:
a first connector, comprising:
   a first connector body with a first inlet configured to be coupled to a first portion of tubing and a first outlet in fluid communication with the first inlet; and
   a collar disposed between the first inlet and the first outlet;
a second connector, comprising:
   a second connector body with a second inlet configured to be releasably coupled with the first outlet of the first connector, and a second outlet threadedly engaged with a second portion of tubing and in fluid communication with the second inlet; and
   a shoulder disposed between the second inlet and the second outlet; and
a coupler, comprising:
   a coupler body comprising a first end and a second end, and defining a cavity, wherein the first connector and the second connector are at least partially disposed within the cavity;
   a plurality of first retaining fingers, wherein the plurality of first retaining fingers are biased to engage against the collar of the first connector to prevent axial motion of the first connector relative to the second connector; and
   a plurality of second retaining fingers, wherein the plurality of second retaining fingers are biased to engage against the shoulder of the second connector with a retention force, and the plurality of second retaining fingers are configured to release the second connector in response to a pullout force exerted on the second connector exceeding the retention force.

8. The coupler assembly of claim 7, wherein at least one of the first connector and the second connector comprises a sealing valve configured to prevent fluid flow in an uncoupled state.

9. The coupler assembly of claim 7, wherein the collar defines a recess extending radially inward.

10. The coupler assembly of claim 7, wherein the first connector body comprises a frustroconical portion disposed between the first inlet and the collar, and the coupler body further comprising a tapered portion within the cavity, wherein the tapered portion is configured to engage with the frustroconical portion to radially align the first connector within the cavity.

11. The coupler assembly of claim 7, wherein each of the plurality of second retaining fingers comprises a ramped protrusion extending radially inward.

12. The coupler assembly of claim 7, wherein the coupler body comprises a tubular shape.

13. The coupler assembly of claim 7, wherein the plurality of first retaining fingers are circumferentially spaced apart.

14. The coupler assembly of claim 7, wherein the plurality of first retaining fingers are configured to permit rotational motion of the first connector relative to the coupler.

15. The coupler assembly of claim 7, wherein each of the plurality of first retaining fingers comprises a protrusion extending radially inward.

16. The coupler assembly of claim 7, wherein the plurality of first retaining fingers extend from a respective plurality of first windows defined in the coupler body.

17. The coupler assembly of claim 7, wherein the plurality of second retaining fingers defines a respective plurality of second windows therebetween.

* * * * *